United States Patent

Allais et al.

[11] 4,337,353
[45] Jun. 29, 1982

[54] NOVEL CARBOXYLIC ACIDS, BENZOYL PHENYL ALKANOIC ACIDS AND USE THEREOF

[75] Inventors: André Allais, Gagny; Francois Clemence, Paris; Jean Meier, La Varenne Saint-Hilaire; Roger Deraedt, Les Pavillons-sous-Bois, all of France

[73] Assignee: Roussel UCLAF, Paris, France

[21] Appl. No.: 875,323

[22] Filed: Feb. 6, 1978

Related U.S. Application Data

[63] Continuation-in-part of Ser. No. 540,382, Jan. 13, 1975, abandoned.

[30] Foreign Application Priority Data

Jan. 24, 1974 [FR] France .............................. 74 02386

[51] Int. Cl.$^3$ ............................................. C07C 59/84
[52] U.S. Cl. .................................... 562/460; 562/426; 560/9; 560/52; 260/399; 260/405.5; 260/410; 260/413; 260/465 K; 260/465 G; 260/501.1; 260/501.15; 260/544 D; 260/544 S; 424/308; 424/317
[58] Field of Search .................. 560/52, 9; 562/460; 424/308, 317

[56] References Cited

U.S. PATENT DOCUMENTS

| | | | |
|---|---|---|---|
| 3,657,430 | 4/1972 | Shen et al. | 562/460 |
| 3,828,093 | 8/1974 | Bays et al. | 560/52 |
| 3,898,275 | 8/1975 | Houlihan | 562/460 |
| 3,931,286 | 1/1976 | Meier et al. | 560/52 |
| 3,931,302 | 1/1976 | Allais et al. | 560/52 |
| 4,027,040 | 5/1977 | Deraedt et al. | 562/460 |

FOREIGN PATENT DOCUMENTS

| | | | |
|---|---|---|---|
| 1584915 | 1/1970 | France | 560/52 |
| 8440M | 7/1971 | France | 560/460 |
| 1164585 | 9/1969 | United Kingdom | 562/460 |

Primary Examiner—Paul J. Killos
Attorney, Agent, or Firm—Hammond & Littell, Weissenberger and Muserlian

[57] ABSTRACT

Novel carboxylic acids of the formula

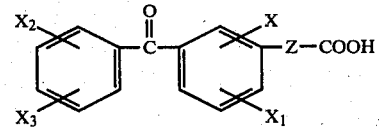

wherein Z is an aliphatic hydrocarbon chain selected from the group consisting of —$(CH_2)_n$— and —CH=CH—$(CH_2)_{n-2}$— where the double bond may be at any point in the chain, n is an integer from 5 to 10 and X, $X_1$, $X_2$ and $X_3$ are individually selected from the group consisting of hydrogen, halogen, alkyl of 1 to 5 carbon atoms, alkoxy of 1 to 5 carbon atoms, alkylthio of 1 to 5 carbon atoms, $CF_3$—, $CF_3O$— and $CF_3S$— and their non-toxic, pharmaceutically acceptable organic and inorganic salts and esters having analgesic and anti-inflammatory activity and their preparation.

3 Claims, No Drawings

NOVEL CARBOXYLIC ACIDS, BENZOYL PHENYL ALKANOIC ACIDS AND USE THEREOF

PRIOR APPLICATION

This application is a continuation-in-part of our co-pending, commonly assigned U.S. patent application Ser. No. 540,382 filed Jan. 13, 1975, now abandoned.

STATE OF THE ART

French BSM Patent No. 8440 M describes benzoyl phenyl acetic acids possessing analgesic and anti-inflammatory properties which have a different structure.

OBJECTS OF THE INVENTION

It is an object of the invention to provide the novel products of formula I and its non-toxic, pharmaceutically acceptable salts and esters.

It is a further object of the invention to provide novel intermediates and a novel process for the preparation of the products of formula I.

It is another object of the invention to provide novel analgesic and anti-inflammatory compositions.

It is an additional object of the invention to provide a novel method of relieving pain and inflammation in humans and other warm-blooded animals.

These and other objects and advantages of the invention will become obvious from the following detailed description.

THE INVENTION

The novel carboxylic compounds of the invention are selected from the group consisting of carboxylic acids of the formula

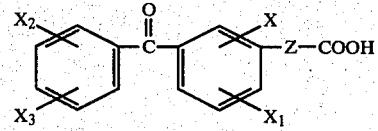

wherein Z is an aliphatic hydrocarbon chain selected from the group consisting of —$(CH_2)_n$— and —C=CH—$(CH_2)_{n-2}$— where the double bond may be at any point in the chain, n is an integer from 5 to 17, preferably 5 to 10 and X, $X_1$, $X_2$ and $X_3$ are individually selected from the group consisting of hydrogen, halogen, alkyl of 1 to 5 carbon atoms, alkoxy of 1 to 5 carbon atoms, alkylthio of 1 to 5 carbon atoms, $CF_3$—, $CF_3O$— and $CF_3S$— and their non-toxic, pharmaceutically acceptable organic and inorganic salts and esters. The X substituents may occupy any position on the ring.

When X, $X_1$, $X_2$ and/or $X_3$ are halogen, they are preferably chlorine or fluorine and when they are alkyl, alkoxy or alkylthio, they are preferably alkyl of 1 to 3 carbon atoms such as methyl, ethyl, n-propyl, methylthio, ethylthio, n-propylthio, methoxy, ethoxy or n-propoxy. When a double bond exists in the hydrocarbon chain of Z, it may be represented as the cis form as well as the trans form.

Examples of suitable salts for the non-toxic, pharmaceutically acceptable salts of the compounds of formula I are alkali metal salts such as sodium, potassium or lithium; alkaline earth metal salts such as calcium; ammonium salt; and amine salts, particularly triloweralkylamines such as triethylamine, diloweralkylamines such as dimethylamine, dipropylamine or diisopropylamine and monoloweralkylamines such as methylamine or ethylamine.

The non-toxic, pharmaceutically acceptable esters of the carboxylic acids of formula I may be those usually used such as hydrocarbon alcohols of 1 to 12 carbon atoms optionally containing hydroxy and/or hetero oxygen atoms.

The preferred esters are especially the esters of alkyls having 1 to 5 carbon atoms, of 2,3-dihydroxypropyl, of isopropylidene 2,3-dioxypropyl, of pivaloyloxymethyl and of geranyl.

A preferred group of compounds of formula I are those where $X_1$ and $X_3$ are hydrogen, $X_2$ is halogen and X is alkyl of 1 to 5 carbon atoms. $X_2$ is preferably chlorine and X is methyl in this instance.

Particularly interesting are the compounds of the formula

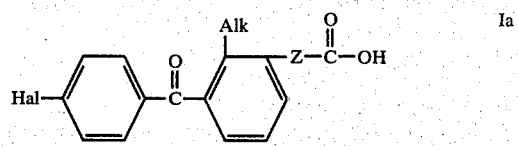

wherein Hal is a halogen and Alk is alkyl of 1 to 5 carbon atoms and Z is as above and their non-toxic, pharmaceutically acceptable salts and esters. Among these compounds are 6-[3'-(4-chlorobenzoyl)-2'-methyl-phenyl]-hexanoic acid, 6-[3'-(4-chlorobenzoyl)-2'-methyl-phenyl]-hex-4-enoic acid, 8-[3'-(4-chlorobenzoyl)-2'-methyl-phenyl]-octanoic acid and 7-[3'-(4-chlorobenzoyl)-2'-methyl-phenyl]-heptanoic acid.

The novel process of the invention for the preparation of compounds of formula I comprises effecting a Wittig reaction with a compound of the formula

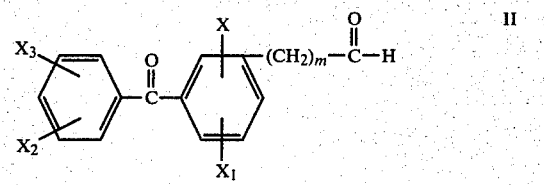

wherein X, $X_1$, $X_2$ and $X_3$ have the above definitions and m is a number from 0 to 15 and a compound of the formula $$(C_6H_5)_3-P=(CH_2)_p-COOR_1 \quad III$$

wherein $R_1$ is hydrogen or lower alkyl of 1 to 7 carbon atoms and p is a number from 0 to 15 and the sum of m+p=n−2 wherein n is the integer of formula I to form a compound of the formula

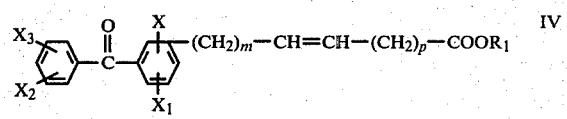

which is a compound of formula I where Z contains a double bond and this product may be salified to form the salt, esterified if $R_1$ is hydrogen or if $R_1$ is alkyl, transesterified or sponified to the acid. The compound of formula IV may be subjected to catalytic hydrogenation to form the corresponding compound of formula I where Z is polymethylene and the product may be treated as the compound of formula IV.

The Wittig reaction may be effected in an organic solvent such as benzene, toluene, tetrahydrofuran or dimethylsulfoxide. It is equally advantageous to form the compound of formula III in situ in an anhydrous mixture of dimethylsulfoxide and tetrahydrofuran and effect the Wittig reaction in the same solvent.

The catalytic hydrogenation may be effected by the hydrogenation of the products of formula IV in a solvent such as methanol or ethanol in the presence of a catalyst such as Raney nickel or platinum oxide.

The compounds of formula II where m is 0 may be prepared by reacting a compound of the formula

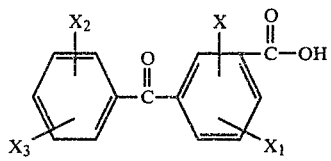

wherein X, $X_1$, $X_2$ and $X_3$ have the above definition which can be prepared by the process of French Patent No. 2,085,638 with thionyl chloride followed by a catalytic reduction in the presence of palladized barium sulfate using the Rosenmund method to obtain a novel compound of the formula

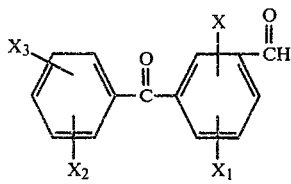

The compounds of formula II wherein m is 1 may be prepared by reacting a compound of the formula

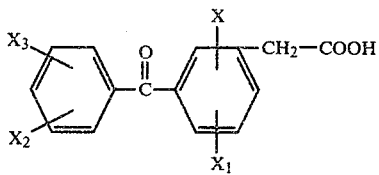

wherein the X's have the above definitions which can be prepared by the process of French BSM Patent No. 8440 M in the same manner as the compound of formula V to obtain a compound of formula II where m is 1.

The products of formula II where m is 2 to 15 are prepared by reacting a compound of formula IIa with a compound of formula III where p is 0 to 13 and $R_1$ is hydrogen or lower alkyl, changing the resulting product to the acid by saponification if $R_1$ is alkyl and reacting the latter as with the compounds of formula V to obtain the desired product.

The compounds of formula III that are not known may be prepared by reacting a strong base with a compound of the formula

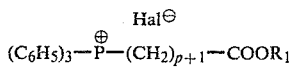

where p and $R_1$ have the definitions of formula III and Hal is a halogen. The compounds of formula VI which are not known may be prepared by reacting a compound of the formula

wherein p, $R_1$ and Hal have the above definitions with triphenylphosphine in an anhydrous solvent such as ether, benzene, toluene or xylene or in the absence of a solvent.

A modification of the process of the invention to prepare compounds of formula I wherein Z is —(CH$_2$)$_4$— or —CH$_2$—CH=CH—CH$_2$— comprises reacting a compound of the formula

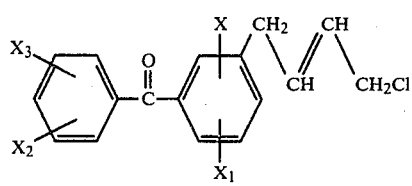

with a cyanogenation agent to obtain a compound of the formula

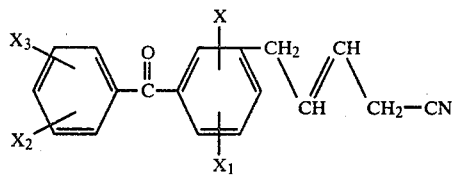

which can be hydrolyzed to the corresponding unsaturated acid of formula I then salified or esterified or the compound of formula IX can be catalytically hydrogenated to form the saturated acid of formula I, which can be salified or esterified.

The cyanogenation is advantageously effected with potassium cyanide in the presence of potassium iodide in anhydrous acetone. The hydrolysis of the cyano group is preferably effected in a mixture of acetic acid, sulfuric acid and water and the hydrogenation is preferably effected in methanol or in the presence of Raney nickel. The products of formula VIII may be prepared by the process of Belgium Patent No. 788,316.

The products of formula I wherein Z is —(CH$_2$)$_5$— or —CH$_2$—CH=CH—CH$_2$—CH$_2$— may be prepared by reacting a compound of formula VIII with an acetic acid ester of the formula

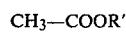

wherein R' is alkyl of 1 to 6 carbon atoms in the presence of cuprous iodide and lithium diisopropylamide in anhydrous tetrahydrofuran to obtain a compound of the formula

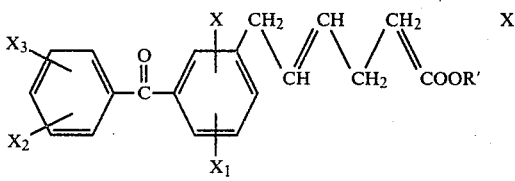

which is an alkyl ester of a compound of formula I wherein Z is —CH$_2$—CH=CH—CH$_2$—CH$_2$— which can be saponified to obtain a compound of formula I wherein Z is —CH$_2$—CH=CH—CH$_2$—CH$_2$— which can be salified or esterified, or the compound of formula X may be catalytically hydrogenated to obtain an alkyl ester of a compound of formula I wherein Z is —(CH$_2$)$_5$— which can be saponified to obtain the corresponding acid which can be salified or esterified. The acetic acid ester is preferably ethyl acetate and the hydrogenation is preferably effected with Raney nickel in methanol.

The novel analgesic and anti-inflammatory compositions of the invention are comprised of at least one compound of formula I or its non-toxic, pharmaceutically acceptable salts or esters. The compositions may be in the form of injectable solutions or suspensions, tablets, capsules, gelules, drinkable solutions or emulsions, suppositories, pomades, creams or topical powders prepared in the usual manner.

The compositions have analgesic and anti-inflammatory activity without gastric ulcerogenic side effects and are therefore useful for the treatment of muscular, articulary or nervous pains, rhumatismal affections, dental pains, zonas and migraines.

The novel method of relieving pain and inflammation in humans or animals comprises administering to human or animals an effective amount of at least one compound of formula I or its non-toxic, pharmaceutically acceptable salt or esters. The products may be administered parenterally, orally, rectally or topically to skin or mucus membrane. The usual effective daily dose is 2 to 20 mg/kg depending upon the product and the method of administration.

In the following examples there are described several preferred embodiments to illustrate the invention. However, it is to be understood that the invention is not intended to be limited to the specific embodiments.

EXAMPLE 1

6-[3'-(4-chlorobenzoyl)-2'-methyl-phenyl]-hex-5-enoic acid

STEP A: 2-methyl-3-(4-chlorobenzoyl)-benzaldehyde

A mixture of 43.92 g of 2-methyl-3-(4-chlorobenzoyl)benzoyl chloride [prepared by process of French Patent No. 2,085,638], 450 ml of xylene, 4.5 g of barium sulfate containing 10% palladium and 0.4 ml of a solution prepared by refluxing 6 g of quinoline and 1 g of sulfur for 5 hours and diluting the product with 70 ml of xylene after cooling was stirred for 45 minutes at 130° C. while passing hydrogen therethrough. The mixture was stirred at 130° C. until hydrochloric acid evolution ceased and was then allowed to cool to 30° C. while passing an inert gas therethrough. The catalyst was removed by filtration and the solvent was evaporated from the filtrate. The oily residue was taken up in isopropyl ether and after adding sodium bisulfite thereto, the mixture was stirred for 18 hours. The precipitated bisulfite was removed by vacuum filtration, was washed and then was decomposed by stirring for 2½ hours under an inert gas in the presence of ether and dilute sulfuric acid. The ether was decanted and the aqueous phase was extracted again with ether. The combined ether phases were washed with water, dried and the ether was evaporated under reduced pressure. The residue was crystallized from isopropyl ether to obtain 24.3 g of 2-methyl-3-(4-chlorobenzoyl)-benzaldehyde melting at 68° C.

Analysis: C$_{15}$H$_{11}$ClO$_2$; molecular weight=258.70. Calculated: %C, 69.63; %H, 4.29; %Cl, 13.71. Found: C, 69.4; H, 4.3; Cl, 13.7.

STEP B:

6-[3'-(4-chlorobenzoyl)-2'-methyl-phenyl]-hex-5-enoic acid

A mixture of 3.52 g of a 60% oily suspension of sodium hydride and 20 ml of a 1:1 dimethylsulfoxide-tetrahydrofuran mixture cooled to −2° C. was stirred for 33 minutes while adding thereto a solution of 10.34 g of 2-methyl-3'-(4-chlorobenzoyl)-benzaldehyde and 18.6 g of ω-carboxybutyl triphenyl phosphonium bromide in 100 ml of dimethylsulfoxide and then 100 ml of tetrahydrofuran were added. The mixture was stirred for 2 hours at 0° to −3° C. and then at room temperature for 15 hours and the solvent was removed. The residue was added to water and after 178 hour, the triphenylphosphine oxide formed was filtered off. The filtrate was mixed with activated carbon which was then filtered off. The filtrate was acidified with concentrated hydrochloric acid and the oily precipitate was extracted with ether. The ether phase was washed with water containing sodium chloride, dried in the presence of activated carbon and filtered. The filtrate was evaporated to dryness and the oily residue was twice chromatographed over silica with a 95:5 methylene chloride-methanol eluate and the second time with 1:1:0.1 cyclohexane-ethyl acetate-acetic acid mixture to obtain 8.97 g of 6-[3'-(4-chlorobenzoyl)-2'-methyl-phenyl]-hex-5-enoic acid having an Rf=0.39 in the second solvent system.

Analysis: C$_{20}$H$_{19}$ClO$_3$; molecular weight=342.807. Calculated: %C, 70.07; %H, 5.59; %Cl, 10.34. Found: C, 70.1; H, 5.7; Cl, 10.6.

EXAMPLE 2

6-[3'-(4-chlorobenzoyl)-2'-methyl-phenyl]-hex-4-enoic acid STEP A: ethyl 6-[3'-(4-chlorobenzoyl)-2'-methyl-phenyl]-hex-4-enoate 21.6 ml of a solution of butyllithium in hexane titrating 1.85 moles per liter were added under an inert atmosphere over 15 minutes at 15° C. to a mixture of 5.62 ml of diisopropylamine and 50 ml of tetrahydrofuran to obtain a solution of lithium diisopropylamide. The said solution was added over 40 minutes under an inert atmosphere to a mixture of 3.9 ml of ethyl acetate, 15.2 g of cuprous iodide and 150 ml of tetrahydrofuran cooled to −100° C. and the temperature was then allowed to rise to −30° C. in 20 minutes. 6.4 g of 1-chloro-4-[3'-(4-chlorobenzoyl)-2'-methyl-phenyl]-but-2-ene in 50 ml of tetrahydrofuran were added thereto at −30° C. over 40 minutes and after returning the temperature to 20° C., 4 ml of a saturated ammonium chloride solution were added. The mixture was vacuum filtered and the filtrate was evaporated to dryness. The residue was taken up in methylene-chloride and the solution was filtered. The filtrate was washed with a sodium thiosulfate solution and then with water, dried over magnesium sulfate and treated with activated carbon. The mixture was filtered and the filtrate was evaporated to dryness to obtain 7.36 g of a reddish-brown oil with an Rf=0.43 (CH$_2$Cl$_2$ eluant) which was ethyl 6-[3'-(4-chlorobenzoyl)-2'-methyl-phenyl]-hex-4-enoate.

STEP B:
6-[3'-(4-chlorobenzoyl)-2'-methyl-phenyl]-hex-4-enoic acid

A mixture of 14.6 g of raw ester of Step A, 100 ml of methanol and 10 ml of water in the presence of 5.2 ml of sodium hydroxide was stirred under an inert atmosphere at 20° C. and the methanol was distilled. The residue was taken up in water and the solution was treated with activated carbon, was filtered and acidified with concentrated hydrochloric acid. The mixture was extracted with ether and the ether phase was washed with water, dried over magnesium sulfate, treated with activated carbon filtered. The filtrate was evaporated to dryness and the residue was chromatographed over silica and eluted with a 95-5 methylene chloride-methanol mixture to obtain 7.58 g of 6-[3'-(4-chlorobenzoyl)-2'-methyl-phenyl]-hex-4-enoic acid melting at 73° C.

Analysis: $C_{20}H_{19}ClO_3$; molecular weight=342.8. Calculated: %C, 70.07; %H, 5.59; %Cl, 10.34. Found: C, 70.4; H, 5.8; Cl, 10.3.

EXAMPLE 3
6-[3'-(4-chlorobenzoyl)-2'-methyl-phenyl]-hexanoic acid

Hydrogen was passed through a mixture of 16.27 g of 6-[3'-(4-chlorobenzoyl)-2'-methyl-phenyl]-hex-4-enoic acid in 80 ml of methanol and 16.3 g of Raney nickel and then the catalyst was filtered off. The methoanol was distilled from the filtrate and the residue was taken up in methylene chloride. The solution was dried, treated with activated carbon, filtered and evaporated to dryness to obtain, after crystallization from a 1-1 isorpopyl ether-petroleum ether mixture, 11.15 g of 6-[3'-(4-chlorobenzoyl)-2'-methyl-phenyl]-hexanoic acid melting at 82° C.

Analysis: $C_{20}H_{21}ClO_3$; molecular weight=344.84 Calculated: %C, 69.66; %H, 6.14; %Cl, 10.28. Found: C, 70.0; H, 6.1; Cl, 10.3.

EXAMPLE 4
6-[3'-(4-chlorobenzoyl)-2'-methyl-phenyl]-hexanoic acid 5.425 g of 6-[3'-(4-chlorobenzoyl)-2'-methyl-phenyl]-hex-5-enoic acid dissolved in 100 ml of ethanol in the presence of 110 mg of platinum oxide had hydrogen pased therethrough and then the catalyst was filtered off. The filtrate was evaporated to dryness and the residue was taken up in ether. The solution was treated with activated carbon, filtered and evaporated to dryness. The residue was crystallized from a 1:1 isopropyl ether-petroleum ether mixture to obtain 4.34 g of 6-[3'-(4-chlorobenzoyl)-2'-methyl-phenyl]-hexanoic acid melting at 82° C.

Analysis: $C_{20}H_{21}ClO_3$; molecular weight=344.822. Calculated: %C, 69.66; %H, 6.14; %Cl, 10.28. Found: C, 69.7; H, 6.2; Cl, 10.1.

EXAMPLE 5
6-[3'-(4-chlorobenzoyl)-2'-methyl-phenyl]-hex-2-enoic acid

Using the procedure of Example 2, 10 g of 4-[3'-(4-chlorobenzoyl)-2'-methyl-phenyl]-butyric acid chloride [described in Belgium Patent No. 788.316] were reacted to form 7.25 g of 4-[3'-(4-chlorobenzoyl)-2'-methylphenyl]-butyraldehyde in the form of an oil.

Analysis: $C_{18}H_{17}ClO_2$; molecular weight=300.77. Calculated: %C, 71.88; %H, 5.7; %Cl, 11.79. Found: C, 72.4; H, 5.8; Cl, 11.6.

A mixture of 4.5 g of the said butyraldehyde and 5.48 g of carbethoxy methylene triphenyl phosphorane in 100 ml of toluene was refluxed under an inert atmosphere with stirring for 17 hours and the toluene was then evaporated. The residue was saponified with 30 ml of 2 N sodium hydroxide and 50 ml of methanol at 75°–80° C. and the methanol was then removed. Water was added to the mixture which was then washed with ether containing 20% of methylene chloride, was treated with activated carbon and filtered. The filtrate was acidified with concentrated hydrochloric acid and was extracted with ether. The ether extracts were treated with activated carbon, filtered and evaporated to dryness. The residue was chromatographed over silica and eluted with a 95:5 methylene chloride-methanol mixture. The product was crystallized from isopropyl ether to obtain 2.015 g of 6-[3'-(4-chlorobenzyl)-2'-methylphenyl]-hex-2-enoic acid melting at 115° C.

Analysis: $C_{20}H_{19}ClO_3$; molecular weight=342.802. Calculated: %C, 70.07; %H, 5.59; %Cl, 10.34. Found: C, 69.9; H, 5.6; Cl, 10.3.

EXAMPLE 6
7-[3'-(4-chlorobenzoyl)-2'-methyl-phenyl]-heptanoic acid

STEP A:
7-[3'-(4-chlorobenzoyl)-2'-methyl-phenyl]-hept-6-enoic acid

A mixture of 16 g of 6-chlorohexanoic acid, 27.8 g of triphenylphosphine and 80 ml of xylene was refluxed for 24 hours and then the xylene was removed. The residue was taken up in methylene chloride and ether was added thereto with stirring The mixture was filtered and the precipitate was dried to obtain 24.6 g of ω-carboxypentyl triphenylphosphonium chloride melting at 165° C.

A solution of 2.585 g of 2-methyl-3-(4-chlorobenzoyl)benzaldehyde and 4.33 g of ω-carboxypentyl triphenyl phosphonium chloride in 70 ml of a 1:1 dimethylsulfoxide-tetrahydrofuran was added with stirring in 5 minutes to 0.885 g of a 60% oily suspension of sodium hydride in 10 ml of a 1:1 dimethylsulfoxide-tetrahydrofuran mixture cooled to 1° C. and the mixture was stirred at 0° C. for 2 hours and at room temperature for 16 hours. The solvents were removed and the residue was taken up in dilute sodium hydroxide. The solution was extracted with ether containing 20% of methylene chloride and the ether extracts were washed with 0.5 N sodium hydroxide. The combined alkaline aqueous phases were acidified with concentrated hydrochloric acid and extracted with ether. The ether extracts were dried in the presence of activated carbon, filtered and evaporated to dryness to obtain 3.35 g of amorphous 7-[3'-(4-chlorobenzoyl)-2'-methyl-phenyl]-hept-6-enoic acid with an Rf=0.7 (8:2 methylene chloride-ethanol mixture) which was used as in for the next step.

STEP B:
7-[3′-(4-chlorobenzoyl)-2′-methyl-phenyl]-heptanoic acid

Hydrogen was passed through a solution of 3.35 g of the acid Step A in 25 ml of methanol in the presence of 67 mg of platinum oxide and then the mixture was filtered. The filtrate was evaporated to dryness and the residue was dissolved in 2 N sodium hydroxide. The solution was washed with ether, treated with activated carbon, filtered and acidified with concentrated hydrochloric acid. The oily precipitate was extracted with ether and the extracts were concentrated to dryness. The residue was chromatographed over silica and was eluted with 9:1 methylene chloride-methanol mixture. The product was crystallized from isopropyl ether to obtain 1.305 g of 7-[3′-(4-chlorobenzoyl)-2′-methyl-phenyl]-heptanoic acid melting at 84° C.

Analysis: $C_{21}H_{23}ClO_3$; molecular weight=358.8. Calculated: %C, 70.28; %H, 6.46; %Cl, 9.88. Found: C, 70.4; H, 6.6; Cl, 9.8.

EXAMPLE 7
8-[3′-(4-chlorobenzoyl)-2-methyl-phenyl]-octanoic acid

STEP A:
8-[3′-(4-chlorobenzoyl)-2′-methyl-phenyl]-oct-7-enoic acid

A mixture of 10.21 g of ethyl ω-bromoheptanoate, 11.3 g of triphenylphosphine and 10 ml of anhydrous ether was stirred for 7 days at 37° C. and was then filtered. The precipitate was washed with ether and dried under reduced pressure to obtain 21.8 g of amorphous ω-carboxyhexyl triphenyl phosphonium bromide.

Analysis: $C_{27}H_{32}BrO_2P$; molecular weight=499.48. Calculated: %C, 64.92; %H, 6.46; %Br, 16.00; %P, 6.21. Found: C, 65.3; H, 6.5; Br, 15.7; P, 6.3.

A solution of 2.585 g of 2-methyl-3-(4-chlorobenzoyl)benzaldehyde and 5.49 g of ω-carbethoxyhexyl triphenyl phosphonium bromide in 25 ml of a 1:1 dimethylsulfoxidetetrahydrofuran mixture was added with stirring in 3 minutes to 520 mg of a 60% oil suspension of sodium hydride in 15 ml of a 1:1 dimethylsulfoxide-tetrahydrofuran mixture cooled to 2° C. and stirring was continued for 16 hours at 24° C. after the temperature had risen. The mixture was then cooled to 5° C. and 2 ml of acetic acid were added thereto. The solvents were removed and the residue was empasted with isopropyl ether and then filtered to remove insolubles. The filtrate was evaporated and the residue was saponified in a mixture of 50 ml of methanol and 15 ml of a 2 N sodium hydroxide solution at 80° C. for 1 hour. The methanol was removed and water was added. The mixture was extracted with ether and the aqueous phase was treated with activated carbon, filtered and acidified with concentrated hydrochloric acid. The oily residue was extracted with ether and the ether phase was washed with water, dried over magnesium sulfate, filtered and concentrated to dryness to obtain 2.98 g of 8-[3′-(4-chlorobenzoyl)-2′-methyl-phenyl]-oct-7-enoic acid with an Rf=0.35 (8:2 $CH_2Cl_2$-acetone mixture).

STEP B:
8-[3′-(4-chlorobenzoyl)-2′-methyl-phenyl]-octanoic acid

Hydrogen was passed through a solution of 2.98 g of the acid of Step B in 40 ml of methanol in the presence of 3 g of Raney nickel and the mixture was then filtered. The filtrate was evaporated to dryness and the amorphous residue was dissolved in 50% sodium carbonte. The solution was treated with activated carbon, filtered and acidified with concentrated hydrochloric acid. The resulting crystals were crystallized from hexane to obtain 2.275 g of 8-[3′-(4-chlorobenzoyl)-2′-methyl-phenyl]-octanoic acid melting at 70° C.

Analysis: $C_{22}H_{25}ClO_3$; molecular weight=372.877. Calculated: %C, 70.86; %H, 6.76; %Cl, 9.51. Found: C, 71.2; H, 6.8; Cl, 9.3.

EXAMPLE 8
10-[3′-(4-chlorobenzoyl)-2′-methyl-phenyl]-decanoic acid

STEP A:
10-[3′-(4-chlorobenzoyl)-2′-methyl-phenyl]-dec-9-enoic acid

A mixture of 35.34 g of triphenylphosphine in 120 ml of anhydrous benzene and 34.85 g of ethyl ω-iodononanoate was refluxed for 21½ hours and then the benzene was removed. The residue was washed with ether and dried under reduced pressure to obtain 63 g of ω-carbethoxyoctyl triphenylphosphonium iodide which was used as is for the next step.

A solution of 16.44 g of ω-carbethoxyoctyl triphenylphosphonium iodide and 5.17 g of 2-methyl-3-(4-chlorobenzoyl)-benzaldehyde in 150 ml of a 1:1 dimethylsulfoxidetetrahydrofuran mixture was added with stirring over 10 minutes to a mixture of 0.960 g of a 60% oil suspension of sodium hydride in 20 ml of a 1:1 dimethylsulfoxide-tetrahydrofuran mixture cooled to 0° C. and the mixture was stirred at 0° C. for 3 hours and at 23° C. for 16 hours. The solvents were removed under reduced pressure and the residue was taken up in boiling isopropyl ether. The solution was cooled to 0° C. and filtered to remove the crystals formed. The filtrate was evaporated to dryness and the residue was saponified with stirring in 30 ml of 2 N sodium hydroxide and 100 ml of methanol at 75° C. for 1½ hours. The solvent was removed and water was added. The mixture was treated with activated carbon and filtered. The filtrate was acidified with concentrated hydrochloric acid and was extracted with ether. The ether phase was treated with activated carbon, filtered and concentrated to dryness. The residue was chromatographed over silica and eluted with a 1:1:0.1 mixture of cyclohexane-ethyl acetate-acetic acid to obtain 6.9 g of an oil which was 10-[3′-(4-chlorobenzoyl)-2′-methylphenyl]-dec-9-enoic acid and was used as is for the next step.

STEP B:
10-[3′-(4-chlorobenzoyl)-2′-methyl-phenyl]-decanoic acid

Hydrogen was passed through a solution of 6.89 g of the acid of Step A in 100 ml of ethanol in the presence of 140 mg of platinum oxide for 45 minutes and the mixture was then filtered. The filtrate was evaporated to dryness and the residue was treated with ether in the presence of activated carbon and was crystallized from a 1:1 isopropyl ether-petroleum ether mixture to obtain 5.56 g of 10-[3′-(4-chlorobenzoyl)-2′-methyl-phenyl]-decanoic acid melting at 74° C.

Analysis: $C_{24}H_{29}ClO_3$; molecular weight=400.93. Calculated: %C, 71.89; %H, 7.29; %Cl, 8.84. Found: C, 71.8; H, 7.2; Cl, 8.6.

EXAMPLE 9

12-[3'-(4-chlorobenzoyl)-2'-methyl-phenyl]-dodecanoic acid

STEP A:
12-[3'-(4-chlorobenzoyl)-2'-methyl-phenyl]dodec-11-enoic acid

A mixture of 5.3 g of 11-bromoundecanoic acid and 5.24 g of triphenylphosphine was heated with stirring at 90° C. for 1 hour and after cooling, the mixture was taken up in a 20:1 chloroform-ethanol mixture. 5 ml of ether were added thereto and the organic phase was decanted. The residue was dried to a constant weight under reduced pressure to obtain 6.6 g of ω-carbethoxydecyl triphenyl phosphonium bromide which was used as is.

Analysis: $C_{29}H_{36}BrO_2P$; molecular weight = 527.44. Calculated: %C, 66.03; %H, 6.88; %Br, 15.15; %P, 5.87. Found: C, 66.5; H, 7.1; Br, 15.5; P, 5.5.

A solution of 6.17 g of ω-carbethoxydecyl triphenyl phosphonium bromide and 3.12 g of 2-methyl-3-(4-chlorobenzoyl)-benzaldehyde in 68 ml of a 1:1 dimethylsulfoxide-tetrahydrofuran mixture was added with stirring over 5 minutes to 1.07 g of a 60% oily suspension of sodium hydride in 10 ml of a 1:1 dimethylsulfoxide-tetrahydrofuran mixture cooled to 0° C. and the mixture was stirred at 0° C. for 2 hours and at room temperature for 16 hours. The mixture was evaporated to dryness and the residue was taken up in water. The solution was washed with ether and was acidified with concentrated hydrochloric acid and extracted with ether. The ether extracts were dried, treated with activated carbon, filtered and evaporated to dryness. The residue was chromatographed over silica and was eluted with an 85:15 methylene chloride-acetone mixture. The product was crystallized from pentane to obtain 2.68 g of 12-[3'-(4-chlorobenzoyl)-2'-methyl-phenyl]-dodec-11-enoic acid melting at 49° C.

Analysis: $C_{26}H_{31}ClO_3$; molecular weight = 426.98 Calculated: %C, 73.13; %H, 7.31; %Cl, 8.30. Found: C, 73.3; H, 7.4; Cl, 8.6.

STEP B:
12-[3'-(4-chlorobenzoyl)-2'-methyl-phenyl]-dodecanoic acid

Hydrogen was passed through a solution of 2.07 g of the acid of Step A in 60 ml of methanol in the presence of 3 g of Raney nickel for 2 hours and the mixture was then filtered. The filtrate was evaporated to dryness and the residue was crystallized from isopropyl ether to obtain 1.328 g of 12-[3'-(4-chlorobenzoyl)-2'-methyl-phenyl]-dodecanoic acid melting at 79° C.

Analysis: $C_{26}H_{33}ClO_3$; molecular weight = 429. Calculated: %C, 72.79; %H, 7.75; %Cl, 8.26. Found: C, 73.0; H, 7.9; Cl, 8.2.

EXAMPLE 10

9-[3'-(4-chlorobenzoyl)-2'-methyl-phenyl]-nonanoic acid

STEP A:
9-[3'-(4-chlorobenzoyl)-2'-methyl-phenyl]-non-8-enoic acid

A mixture of 20 g of ethyl ω-bromooctanoate, 22.9 g of triphenylphosphine and 200 ml of anhydrous xylene was refluxed under a nitrogen atmosphere for 18 hours and after cooling to room temperature, the solvent was distilled off. The residue was empasted with anhydrous ether and dried under reduced pressure to obtain 30.95 g of ω-carbethoxyheptyl triphenyl phosphonium bromide in the form of a colorless gum.

Analysis: $C_{28}H_{34}BrO_2P$; molecular weight = 513.50. Calculated: %C, 65.49; %H, 6.67; %Br, 15.57; %P, 6.04. Found: C, 65.4; H, 6.8; Br, 15.7; P, 6.0.

A solution of 5.17 g of 2-methyl-3-(4-chlorobenzoyl)-benzaldehyde and 10.27 g of ω-carbethoxyheptyl triphenyl phosphonium bromide in 150 ml of a 1:1 dimethylsulfoxide-tetrahydrofuran mixture was added with stirring over 15 minutes to 0.92 g of a 60% suspension of sodium hydride in 20 ml of a 1:1 dimethylsulfoxide-tetrahydrofuran mixture cooled to 0° C. and the mixture was stirred at 3° C. for 15 minutes and then at room temperature for 18 hours. The solvents were evaporated under reduced pressure and the gummy residue was taken up in hot isopropyl ether. The solvent was evaporated and the residue was taken up in 20 ml of 2 N sodium hydroxide and 60 ml of methanol. The methanol was distilled off and 100 ml of water and 500 mg of activated carbon were added thereto. The mixture was filtered and the filtrate was washed with 0.5 N sodium hydroxide and then water and acidified with concentrated hydrochloric acid. The mixture was extracted with ether and the ether phase was washed with water, dried over magnesium sulfate in the presence of activated carbon, filtered and evaporated to dryness to obtain 6.59 g of 9-[3'-(4-chlorobenzoyl)-2'-methyl-phenyl]-non-8-enoic acid in the form of a pale yellow amorphous product which was used as is for the next step.

STEP B:
9-[3'-(4-chlorobenzoyl)-2'-methyl-phenyl]-nonanoic acid

Hydrogen was passed through a solution of 6.3 g of the acid of Step A in 100 ml of ethanol in the presence of 120 mg of platinum oxide and after the absorption of 3.86 ml of hydrogen, the mixture was filtered. The filtrate was evaporated to dryness and the 6.3 g of raw product were dissolved in 10 ml of hot isopropyl ether to which 10 ml of petroleum ether were then added. The mixture stood at room temperature, was iced and vacuum filtered. The precipitate was washed with a 1:1 isopropyl ether-petroleum ether mixture and was dried under reduced pressure to obtain 5.535 g of 9-[3'-(4-chlorobenzoyl)-2'-methyl-phenyl]-nonanoic acid melting at 64° C.

Analysis: $C_{23}H_{27}ClO_3$; molecular weight = 386.907. Calculated: %C, 71.39; %H, 7.04; %Cl, 9.16. Found: C, 71.6; H, 7.0; Cl, 9.2.

EXAMPLE 11

Tablets were prepared from 100 mg of 6-[3'-(4-chlorobenzoyl)-2'-methyl-phenyl]-hexanoic acid and 250 mg of an excipient of lactose, starch, talc and magnesium stearate.

PHARMACOLOGICAL STUDY

A. Anti-inflammatory Activity

1. Chronic Arthritis of Adjuvant (Preventative Treatment)

The injection of a Freund type adjuvant into the rear paw of a rat provokes the rapid appearance of a primary inflammatory lesion in the paw and then after a latency period of 13 to 15 days, there appears a secondary arthritis in the other rear paw as well as the front paws, the tail and ears. Male rats 42 to 50 days old received an intraplantory injection of 0.1 ml of the Freund type adjuvant which was a suspension of 6 mg of dead mycobacterium butyrium per ml of vaseline oil. The rats received orally the test product on the day of the adjuvant injection and then were observed until the 17th day when they were killed. The control arthritic animals and the control normal animals received only the vehicle. The rating scale for the activity of the test compounds was the augmentation of the volume of the injected and noninjected rear paws as compared to volume of the corresponding paws of the normal controls, the arthritis of the front paws, the tails and ears and the $\alpha_2$ macroglobulin seric ratio. These values were assembled for the total arthritic index and the $DA_{40}$ dose of the test compound which reduced by 40% the arthritic index of the treated animals as compared to the arthritic controls was determined. The results are in Table I.

2. Carraghenin Edema

Rats weighing about 150 g received a single injection of 0.5 mg of carraghenin in the plantary aponevrose of a rear paw to provoke the formation of an inflammatory edema. The test products were orally administered at the same time of the irritant injection and the paw volume was measured before and 5 hours after the irritant injection. The augmentation of volume was the measurement of the inflammation degree and the $DA_{40}$ dose was determined.

B. Analgesic Activity

This test was based on the observations of Koster et al [Fed. Proc., Vol. 18 (1959), p. 412] wherein the intraperitoneal injection of acetic acid provokes in mice characteristic repeated stretching and twisting movements for more than 6 hours. Analgesics suppress or prevent this syndrome and the acetic acid used was diluted with water to a 1% concentration and the dose for releasing this syndrome was 100 mg/kg. The test products were orally administered ½ hour before the acetic acid injection and the mice were not fed since the day before the test. The stretchings were counted for each mouse for an observation period of 15 minutes starting immediately after the injection. The analgesic effect for each dose was expressed as percent of protection as compared to controls and the $DA_{50}$ dose was determined. The results are in Table I.

C. Gastric Ulcergenic Side Effects

This test was effected on rats weighing about 130 g fasting for 24 hours before the start of the test at which time the test products were orally administered. After 7 hours, the degree of the ulcerous lesions in the stomach were evaluated on a scale of 0 to 3 with a value of 1 ($DA_1$) corresponding to an average ulcerogenic dose. The results re reported in Table I.

TABLE I

| | Pharmacological Activity | | | Side effect |
|---|---|---|---|---|
| | Anti-inflammatory | | Analgesic | |
| Compound of Example | Arthritis of adjuvant $DA_{40}$ mg/Kg | edema of carraghenin $DA_{40}$ mg/Kg | Test of acetic acid $DA_{50}$ mg/Kg | Activity ulcergenic gastric $DA_1$ mg/Kg |
| 1 | <10 | 27 | 3 | >500 |
| 2 | 2.5 | 14 | 7 | >500 |
| 4 | 1.5 | 9 | 2 | >500 |
| 5 | <10 | 60 | 3 | >500 |
| 6 | >20 | >200 | 8 | >500 |
| 7 | 3 | 13 | 10 | 400 |
| 8 | 1.5 | 100 | 15 | >500 |
| 9 | 1.5 | >100 | 10 | >500 |

The results of Table I show that the compounds have a very interesting analgesic activity without being ulcergenic and have anti-inflammatory activity with several having a high degree thereof.

The following tests were conducted with 4-(3'-p-chlorobenzoyl-2'-methyl-phenyl)-butyric acid (hereinafter compound A), a compound of Example 5 of U.S. Pat. No. 3,931,302 which has the formula

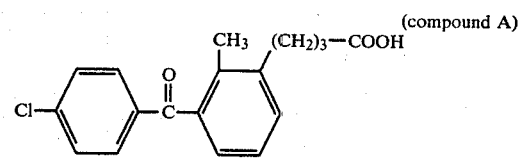
(compound A)

TEST DATA

A. Analgesic Activity

This test was based on the observations of Koster et al [Fed. Proc., Vol. 18 (1959), p. 412] wherein the intraperitoneal injection of acetic acid provokes in mice characteristic repeated stretching and twisting movements for more than 6 hours. Analgesics suppress or prevent this syndrome and the acetic acid used was diluted with water to a 1% concentration and the dose for releasing this syndrome was 100 mg/kg. The test products were orally administered ½ hour before the acetic acid injection and the mice were not fed since the day before the test. The stretchings were counted for each mouse for an observation period for 15 minutes starting immediately after the injection. The analgesic effect for each dose was expressed as percent of protection as compared to controls and the $DA_{50}$ dose was determined. The results are in Table II.

B. Gastric Ulcerogenic Side Effects

This test was effected on rats weighing about 130 g fasting for 24 hours before the start of the test at which time the test products were orally administered. After 7 hours, the degree of the ulcerous lesions in the stomach were evaluated on a scale of 0 to 3 with a value of 1 ($DA_1$) corresponding to an average ulcerogenic dose. The results are reported in Table II.

TABLE II

| | | Side effect | Therapeutic Index |
|---|---|---|---|
| Compound of Example | Analgesic Test of acetic acid $DA_{20}$ mg/kg | Activity gastric ulcerogenic $DA_1$ mg/kg | $\dfrac{DAI}{DA_{50}}$ |
| 1 | 3 | >500 | >166.6 |
| 2 | 7 | >500 | >71.4 |
| 4 | 2 | >500 | >250 |

TABLE II-continued

| Compound of Example | Analgesic Test of acetic acid $DA_{20}$ mg/kg | Side effect Activity gastric ulcerogenic $DA_1$ mg/kg | Therapeutic Index $\dfrac{DA_I}{DA_{50}}$ |
|---|---|---|---|
| 5 | 3 | >500 | >166.6 |
| 6 | 8 | >500 | >62.5 |
| Compound A | 10 | >500 | >50 |

The results of Table II show that the compound A (of U.S. Pat. No. 3,931,302) is less effective in its analgesic activity and possesses the same level of gastric ulcerogenic activity. The results of Table II show further that the therapeutic index of the compound of the above application is greater than that of compound A. The therapeutic index of compound of Example 4 of the present application is five time greater than that of compound A.

Various modifications of the compositions and processes of the invention may be made without departing from the spirit or scope thereof and it is to be understood that the invention is to be limited only as defined in the appended claims.

We claim:

1. A compound selected from the group consisting of 6-[3'-(4-chlorobenzoyl)-2'-methyl-phenyl]-hexanoic acid and its non-toxic, pharmaceutically acceptable salts and esters.

2. An analgesic and anti-inflammatory composition comprising an effective amount of at least one compound of claim 1 and a pharmaceutically acceptable carrier.

3. A method of relieving pain and inflammation in human or animals comprising administering to human or animals an analgesically and anti-inflammatorily effective amount of at least one compound of claim 1.

* * * * *

UNITED STATES PATENT AND TRADEMARK OFFICE
CERTIFICATE OF CORRECTION

PATENT NO. : 4,337,353
DATED : June 29, 1982
INVENTOR(S) : ANDRE ALLAIS ET AL.

It is certified that error appears in the above—identified patent and that said Letters Patent is hereby corrected as shown below:

Column 4, line 13: "$-(CH_2-$" should read -- $-(CH_2)_4-$ --.

Column 4, line 14: Delete "$)_4-$".

Column 5, line 7: "$-(CH_2-$" should read -- $-(CH_2)_5-$ --.

Column 5, line 8: Delete "$)_5-$".

Column 6, line 20: "178 hour" should read -- 1/2 hour --.

Column 14, line 65; Column 15, line 8: "$DA_{20}$ mg/kg" should read -- $DA_{50}$ mg/kg --.

Signed and Sealed this

Nineteenth Day of October 1982

[SEAL]

Attest:

GERALD J. MOSSINGHOFF

Attesting Officer

Commissioner of Patents and Trademarks